United States Patent [19]

Fleury

[11] Patent Number: 5,569,225
[45] Date of Patent: Oct. 29, 1996

[54] BODILY FLUID TEST KIT AND METHOD OF TESTING BODILY FLUIDS

[75] Inventor: Richard L. Fleury, Orland Park, Ill.

[73] Assignee: GKR Industries, Inc., Alsip, Ill.

[21] Appl. No.: 496,761

[22] Filed: Jun. 29, 1995

[51] Int. Cl.$^6$ ..................................................... A61F 1/00
[52] U.S. Cl. ........................ 604/323; 604/317; 604/329; 604/349; 604/411; 128/767
[58] Field of Search .................................... 604/355, 356, 604/317, 323–3, 327–29, 346–9, 411, 334; 128/767

[56] References Cited

U.S. PATENT DOCUMENTS

| | | | |
|---|---|---|---|
| 3,797,734 | 3/1974 | Fleury et al. | 604/317 |
| 4,258,032 | 3/1981 | Mehl . | |
| 4,300,404 | 11/1981 | Mehl et al. . | |
| 4,333,480 | 6/1982 | Villari et al. | 604/317 |
| 4,340,052 | 7/1982 | Dennehey et al. | 604/317 |
| 4,990,145 | 2/1991 | Fleury | 604/317 |
| 5,251,786 | 10/1993 | Sarrine | 604/411 |
| 5,289,858 | 3/1994 | Grabenkort | 604/411 |
| 5,334,180 | 8/1994 | Adolf et al. | 604/411 |
| 5,368,583 | 11/1994 | Fleury . | |
| 5,380,314 | 1/1995 | Herweck et al. | 604/317 |

FOREIGN PATENT DOCUMENTS

| | | | |
|---|---|---|---|
| 0117695 | 9/1984 | European Pat. Off. | 604/317 |

*Primary Examiner*—John G. Weiss
*Assistant Examiner*—Bruce E. Snow
*Attorney, Agent, or Firm*—Baker & McKenzie

[57] ABSTRACT

An improved disposable container is provided for the collection and testing of bodily fluid samples such a urine specimens. The improved disposable container includes a collection bag that is sealably attached to a tubular member equipped with a lower valve means. A protective sleeve surrounds the collection bag and protects both the patients hands as well as the medical technicians hands during transport and handling of the container once the specimen is deposited therein. The lower end of the collection bag includes an injection site through which a technician may obtain a test sample. Specifically, a syringe may be inserted at the injection site and a test sample of fluid may be safely withdrawn through the injection site, through the syringe and into a test tube. The injection site includes a resilient elastomeric membrane which automatically reseals itself after withdrawal of the syringe.

2 Claims, 3 Drawing Sheets

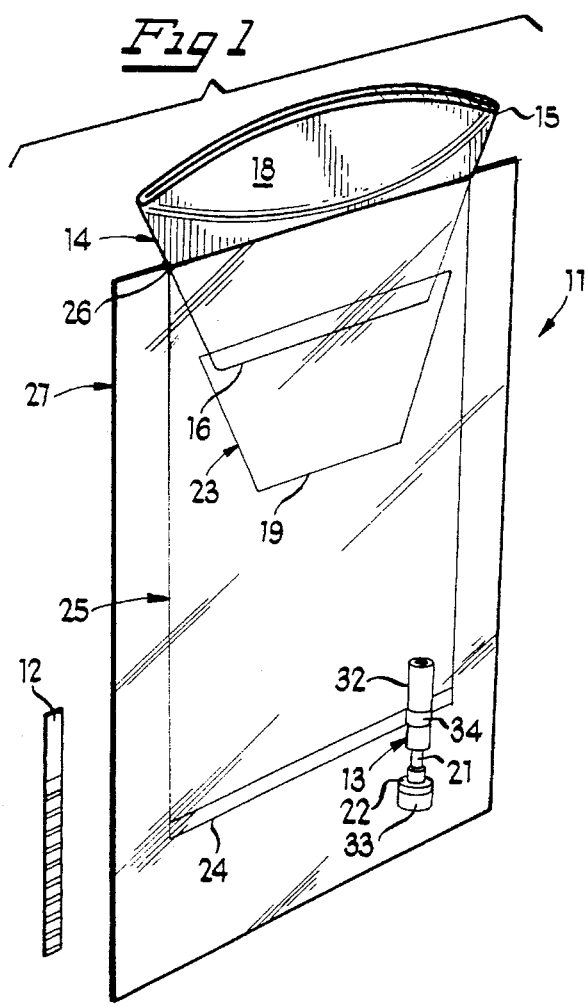
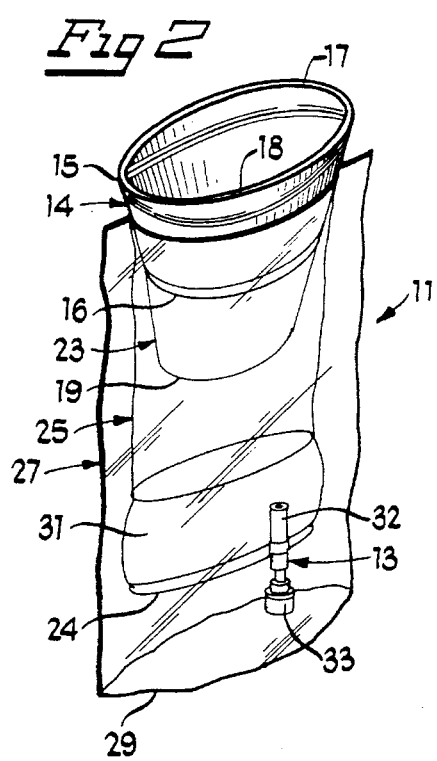
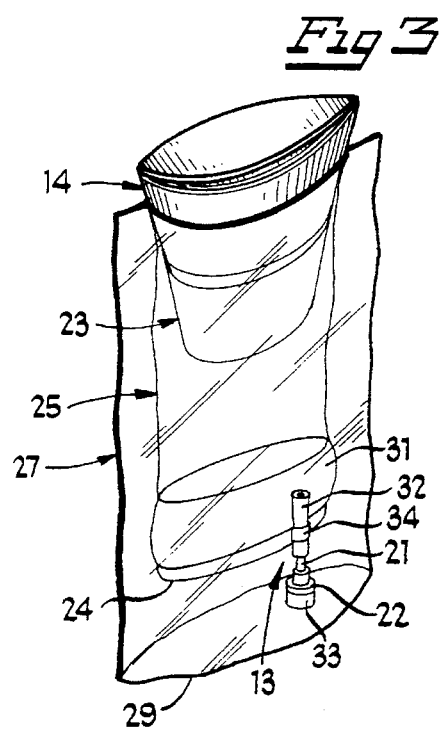
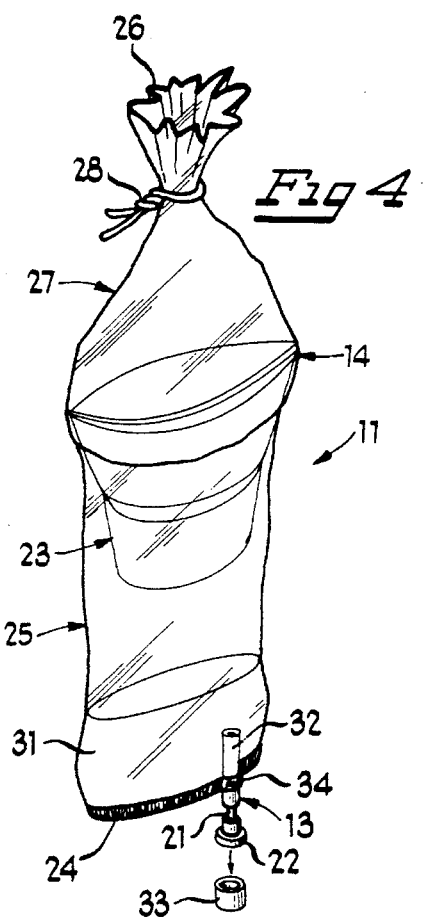

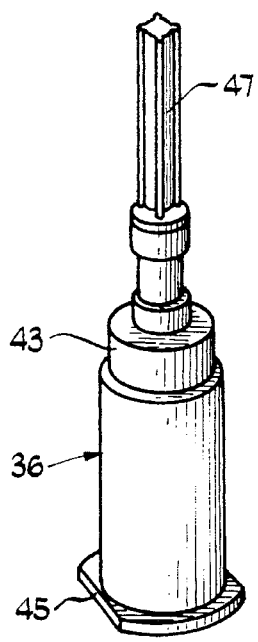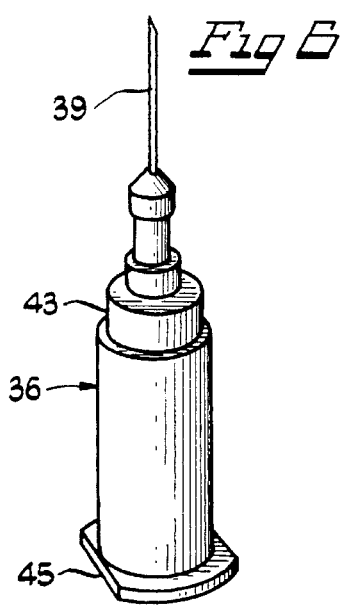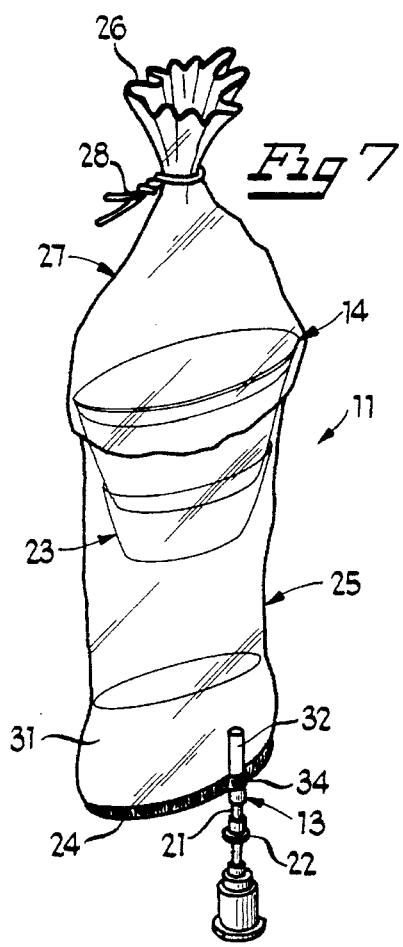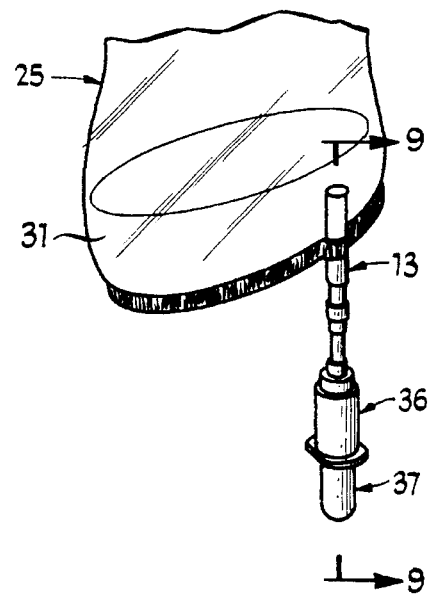

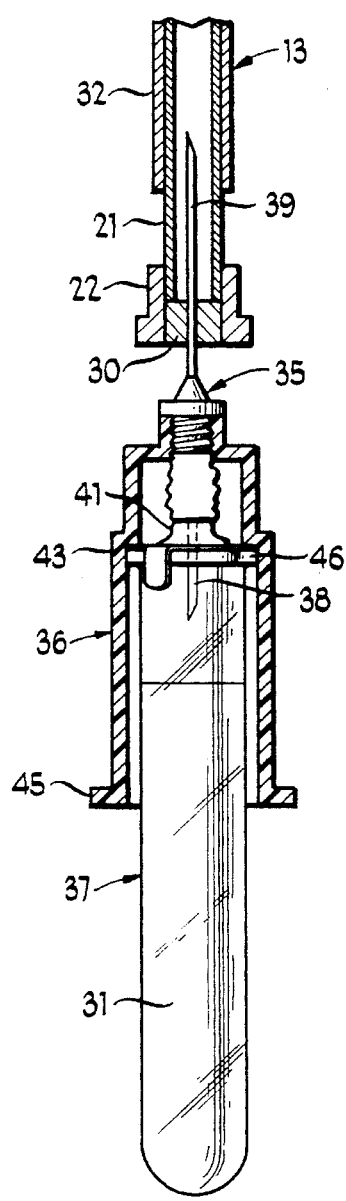
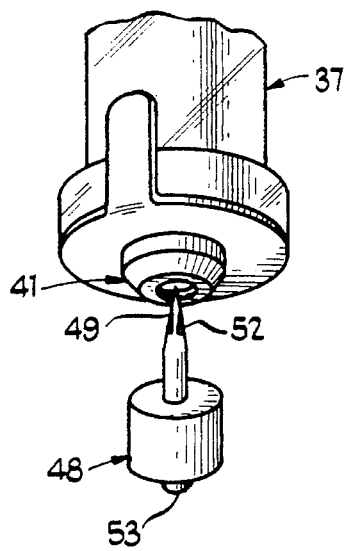
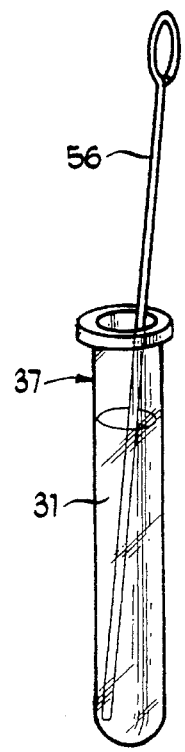
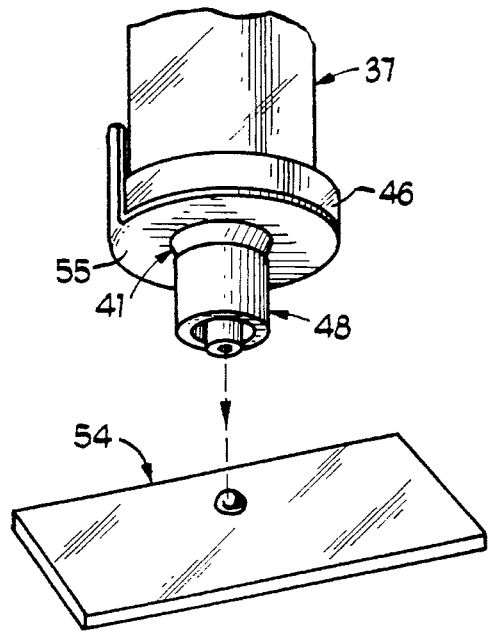

BODILY FLUID TEST KIT AND METHOD OF TESTING BODILY FLUIDS

FIELD OF THE INVENTION

This invention relates generally to a kit for testing bodily fluids and more specifically to a disposable container for accepting bodily fluid specimens that is equipped with a means for safely dispensing test samples of the bodily fluid specimen. Still more specifically, the invention relates to an improved disposable container in which a patient can deposit a bodily fluid specimen in a safe and sanitary manner and further which is equipped with a sealed injection site so that a medical technician can withdraw a test sample of the bodily fluid specimen without danger of exposure to the specimen or unwanted spillage.

BACKGROUND OF THE INVENTION

The concept of disposable containers for the collection of bodily fluid specimens such as urine specimens is well known. U.S. Pat. Nos. 5,368,583 and, 4,990,145 and 3,797,734 all show a disposable bag for collecting bodily fluids. Specifically, the '734 patent shows a bag having a tubular funnel sealingly engaging a plastic bag. The bag is sealably attached over the outer surface of a tubular member. The lower end of the tubular member includes valve means comprised of a flat plastic tube capable of being flattened which allows entry of the fluid downward through the tubular member and into the bag but which prevents fluid from migrating upward and re-entering the tubular member. The '145 patent provides an improvement to the embodiment disclosed in the '734 patent by means of a protective outer sleeve or shroud for protecting the user's skin against fluid contact. As noted in the '145 patent, products made in accordance with both patents have been sold in substantial numbers. Finally, the test kit disclosed in the '583 patent includes the improvements disclosed in the '145 patent and further includes an improved closure means at the upper end of the tubular member which facilitates the deposit of a test strip in the disposable container.

The primary problem with the disposable containers disclosed in the '734, '145 and '583 patents is that there is no safe and, easy means for withdrawing a fluid sample from a filled collection bag for further testing and/or processing. Specifically, while a test strip may be deposited downward into the container disclosed in the '583 patent, there is no easy means for the technician to withdraw a small fluid sample or a test sample from the bag without potentially exposing the technician to fluid contact. Thus, there is still a further need for an improved disposable specimen container from which a test sample may be withdrawn.

It is also imperative that technicians be able to withdraw test samples without danger of spillage or exposure to the fluid test sample. Hepatitis B virus, HIV (Human Immunodeficiency Virus) and other diseases may be transmitted as a result of contact with bodily fluids. Further, the Occupational Safe and Health Administration (OSHA) has issued regulations that medical practices must comply with (see 29 CFR § 1910.1030 et seq.). Thus, there is a need for a disposable specimen container that is easy to use and protects both the patient and medical technician against coming in contact with the bodily fluids and further that enables the medical technician to withdraw a test sample without danger of contact or spillage.

SUMMARY OF THE PRESENT INVENTION

The present invention makes a significant contribution to the disposable medical container art by providing an improved disposable container for accepting and transporting bodily fluids and that further provides a safe and effective means for withdrawing a test sample from said container. The invention features a tubular member with a valve means attached to the lower end of the tubular member. A collection bag is sealably attached to an outer surface of the tubular member. The closed bottom end of the collection bag provides a space for the collection of fluid and the valve means provides a means for containing the fluid in the collection bag and preventing it from spilling upward through the tubular member. An optional sleeve may be sealably attached to the outer surface of the tubular member. During the initial use of the container by the patient, the sleeve is folded downward and provides a shield to protect the patient's hand. The bottom of the collection bag features an injection site which permits the withdrawal of a test sample for testing and processing. In the preferred embodiment, the upper end of the tubular member will include a closure means such as a lid or closure flaps to further preclude any spillage or splatter of the bodily fluid during the transfer between the patient and the nurse or technician.

After the patient has deposited fluid in the collection bag, the patient then hands the container to a nurse or technician who, if a sleeve is employed, will slip his/her hand under the sleeve between the sleeve and the collection bag thereby grasping the container and protecting the nurse's or technician's hand from contact with the bodily fluid. The technician then folds the sleeve upward and over the tubular member and seals the sleeve with a twist-tie or other equivalent sealing means. Then, the technician may withdraw a test sample of the fluid through the injection site provided at the lower end of the collection bag.

In the preferred embodiment, the kit will include a double-ended syringe, mounted onto a test-tube-sleeve and a sealed test tube. The double-ended syringe includes a long end for insertion at the injection site and a short end for insertion into the test tube. The short end is preferably attached to the closed end of the sleeve so that the short end is directed downward through the sleeve and the long end is directed upward away from the sleeve. After the long end of the syringe is inserted at the injection site, the test tube is then inserted through the open end of the sleeve and over the short end of the syringe. The test tube includes a membrane-type seal over its open end which is penetrated by the short end of the syringe as the test tube is inserted upward through the sleeve. The vacuum in the test-tube creates a pressure drop across the syringe thereby causing the test-tube to fill with fluid. A vacuum or low pressure zone is provided inside the test-tube underneath the membrane seal. The membrane may be sealed to the top of the test-tube directly or the membrane may be disposed in the center of a foil-type seal which is attached to the top of the test-tube.

Appropriate safeguards are provided to prevent any spillage of the test sample and further to protect against injury to the technician from either end of the syringe. For example, a cap is provided for the long-end of the syringe. Further, the short end of the syringe is equipped with a latex cover that is simply pushed away as the membrane cover of the test tube is inserted over the short-end of the syringe. The latex or otherwise polymer cover over the short end of the syringe prevents any dripping of fluid from the short-end of the syringe before the test tube is mounted onto the short-end of the syringe.

The construction of the injection site of the collection bag includes a tube which passes through the lower end of the collection bag. The side walls of the tube are sealed against the collection bag and the lower end of the tube preferably includes a membrane-type seal to prevent any premature leakage of fluid through the injection site. The membrane seal is then punctured by the long end of the syringe when the technician is retrieving a test sample. Membrane-type seals are currently available and are apparent to those skilled in the art which are resilient enough to reseal themselves when the syringe is removed. Thus, a fluid sample may be removed through the membrane seal of the injection site and, once the syringe is removed, the membrane reseals itself and prevents any further leakage of fluid. The membrane seal exposed on the tube of the injection site and the membrane seal disposed on top of the test tube may be made of the same or similar materials. The term "septum" may also be used interchangeably with the term "membrane" when describing these types of seals.

In the event the technician desires only a few drops of the sample contained within the test-tube, the kit may further include a piercing sampler which would enable the technician to pierce the seal disposed on type of the test tube for the deposit of one or two drops of fluid onto a glass slide or similar application. A piercing sampler is simply a needle-type device which includes a sharp end for puncturing the membrane seal disposed on the top of a test tube and an open end which enables the fluid to pass through the sharp end of the sampler and out the open end of the sample. The diameter of the open end of the sampler is sufficiently small so that the sampler dispenses single drops at a time. Again, since the membrane seal disposed on top of the test tube is fabricated from resilient elastomeric material which reseals itself upon withdrawn of the piercing sampler from the membrane seal. Preferably, the piercing sampler from the membrane seal. Preferably, the piercing samplers are fabricated from plastic material because they are light weight and can be easily incinerated.

Further, the kit may also include a wire loop which may be inserted downward into the test tube. Wire loops are useful for placing a small amount of sample on a cultured petri dish. In addition, the kit may come equipped with a glass or plastic slide for examination of a drop of fluid specimen under a microscope or similar apparatus.

The present invention also lends itself to an improved methods of collecting and testing bodily fluids. The method includes the patient taking a disposable container in accordance with the present invention and depositing a fluid down through the tubular member and through the valve means and into the collection bag. After the patient has completed depositing the fluid in the bag, the container is handed to the technician. The technician then takes the container by inserting his/her hand upward between the collection bag and the outer sleeve to grasp the tubular member. The technician may then fold the outer sleeve upward over the tubular member and sealably closing the outer sleeve with a twist-tie or other similar sealing mechanism. Then, the technician may withdraw a sample from the injection site by inserting a long-end of a double-ended syringe into the injection site. The opposing end of the syringe is mounted onto a sleeve which can accommodate a test-tube. The technician then inserts a sealed, vacuumed test-tube over the short end of the syringe to draw a fluid sample out of the bag, through the syringe and into the test-tube.

It is therefore an object of the present invention to provide an approved disposable container for accepting, transporting and obtaining test samples of bodily fluids.

Yet another object of the present invention is to provide an improved disposable container for bodily fluid samples that reduces the likelihood of any spillage of bodily fluid during transport, handling or testing of the bodily fluid.

Still another object of the present invention is to provide an approved disposable bodily fluid specimen bag and kit therefore that effectively prevents the possibility of a nurse or medical technician from coming into contact with a patient's bodily fluids thereby helping to prevent the spread of HBV (Hepatitis B Virus) and HIV (Human Immunodeficiency Virus) and further that helps medical practices to comply with the relevant OSHA Regulations (i.e. 37 CFR § 1910.1030 at seq.).

Yet another object of the present invention is to provide an approved kit for the collection and testing of urine specimens from female and male patients.

BRIEF DESCRIPTION OF THE DRAWINGS

This invention is illustrated more or less diagrammatically in the accompanying drawings wherein:

FIG. 1 is a perspective view of a disposable container made in accordance with the present invention;

FIG. 2 is a perspective view of a disposable container made in accordance with the present invention, in an open position;

FIG. 3 is a perspective view of a disposable container made in accordance with the present invention, in a closed position;

FIG. 4 is a perspective view of a disposable container made in accordance with the present invention, particularly illustrating the outer sleeve in a closed position and with the protective cap pulled off of the injection site;

FIG. 5 is a perspective view of a syringe made in accordance with the present invention as attached to a test-tube-holding-sleeve also made in accordance with the present invention;

FIG. 6 is an illustration of a syringe and test-tube-holding-sleeve as made in accordance with the present invention, and as assembled prior to the removal of a sample from the collection bag first shown in FIG. 1;

FIG. 7 is a perspective view of a collection bag, syringe and sleeve prior to the withdrawal of a test sample;

FIG. 8 is an illustration of the syringe, test-tube-holding-sleeve, test-tube and collection bag during the removal of a test sample from the collection bag;

FIG. 9 is a sectional view taken substantially along line 9—9 of FIG. 8;

FIG. 10 is a perspective view of a top of a test-tube and a piercing sampler;

FIG. 11 is a perspective view of the test-tube and piercing sampler shown in FIG. 10 while a drop of sample is being applied to a glass slide; and FIG. 12 is a perspective view of a test-tube, with the cover removed, and with a wire loop inserted therein.

It should be understood that the drawings are not necessarily to scale on details which are necessary for an understanding of the present invention or which render other details are difficult to perceive may have been omitted. It should also be understood, of course, that the invention is not necessarily limited to the particular embodiments illustrated herein.

DETAILED DESCRIPTION OF THE DRAWINGS

Like reference numerals will be used to refer to like or similar parts from Figure to Figure in the following description of the drawings.

The dramatic improvement contributed by the present invention is best understood after consideration of how conventional specimen containers are used. First, the conventional specimen containers which are merely paper or plastic cups are clearly obsolete in light of current concerns over infectious diseases. Accordingly, a truly sealable and disposable specimen container is required. However, of the sealable and disposable specimen containers taught by the prior art, e.g., U.S. Pat. Nos. 5,368,583, 4,990,145 and 3,797,734, there is no safe and convenient way to withdraw a test sample from the container. As seen below, the present invention overcomes this disadvantage by providing a disposable container which is safe and easy to use and which also allows the nurse or medical technician to safely and easily remove a test sample for further processing.

FIG. 1 is an illustration of a disposable container 11, The principle improvement contributed by the container 11 shown in FIG. 1 is the injection site shown generally at 13. The container 11 has five primary parts. The tubular member 14 includes a wide upper end 15 and a narrower lower end 16. Thus, the tubular member 15 functions as a funnel and is easier for women to use. The upper end 15 of the tubular member 14 also features a closure means, which as shown in FIG. 2, includes closure flaps 17 and 18.

Returning to FIG. 1, a valve means 23 is sealably attached to the lower end 16 of the tubular member 14. The lower end 24 of the valve means allows fluid to flow downward through the valve means 23 toward the lower end 24 of the collection bag 25 but does not allow liquid to flow upward through the lower end 24 of the valve means 23 toward the tubular member 14. Thus, the valve means 23 is an effective one-way valve. Fluid may flow downward but cannot flow upward.

The third component of the disposable container 11 is the collection bag 25. The upper end 26 of the collection bag 25 is sealably attached to the tubular member 14. Thus, when fluid is deposited in a lower end 24 of the collection bag 25, the fluid is contained within the collection bag 25 by the effective seal between the upper end 26 of the collection bag 25 around the tubular member 14 and by the effective seal provided at the lower end 19 of the valve means 23.

The fourth primary component of the collection bag 11 is the sleeve or shroud shown at 27. During transport from the patient to the technician, the technician may choose to insert his/her hand up between the collection bag 25 and the shroud 27 thereby utilizing the sleeve 27 as an effective shield against the spillage or splatter of bodily fluid. In addition, as shown in FIG. 4, the sleeve or shroud 27 may be pulled upward over the tubular member and the upper end 26 of the sleeve 27 can be sealed with a twist-tie 28 to provide added insurance against any fluid 31 from leaving the container 11.

Referring to FIGS. 1–4, the fifth component of the container 11 is the injection site 13. In the preferred embodiment, the injection site 13 includes an upper tube 32, a middle tube 21, an end-piece 22, a protective cap 33 (see FIG. 4) and a membrane seal 30 (see FIG. 9). The tube 32 passes through the lower end 24 of the collection bag 25. A seal 34 is provided between the lower end 24 of the collection bag and the tube 32 to prevent any leakage. A membrane or septum-type seal 30 (see FIG. 9) is provided at the end-piece 22 underneath the cap 33 (see FIG. 4) which enables the fluid sample to be drawn out of the collection bag with a syringe or a similar device. The protective cap 33 is intended to protect the membrane seal (not shown).

Turning to FIG. 2, the upper end 15 of the tubular member 14 is substantially wider than the lower end 16 thereby providing a funnel-shaped tubular member 14. Female patients, in particular, appreciate the wider upper member 15. The closure flaps 17, 18 easily fold downward to close the upper end 15 of the tubular end 14 prior to the handing of the container 11 to a nurse or technician (see FIG. 3).

Referring to FIGS. 4–9, the technician may remove a sample of liquid 31 through the injection site 13 with a syringe 35, sleeve 36 and test tube 37 as shown below. Referring now to FIGS. 6 and 9, the syringe 35 includes two ends 38, 39. The short end 38 is for insertion into the top septum or membrane 41 of the test tube 37. The long end 39 is for insertion into the injection site 13 as shown in FIG. 9. The short end 38 of the syringe 35 is preferably inserted into the closed end 43 of the sleeve 36 by the manufacturer and the technician need only to remove the cap 47 prior to insertion of the long-end 39 of the syringe 35 at the injection site 13 as shown in FIG. 7. Once the long-end 39 of the syringe 35 is inserted at the injection site 13, the test tube 37 is pushed upward through the open end 45 of the sleeve 36 and over the short end 38 of the syringe 35 (see FIGS. 8 and 9). Referring to FIG. 9, as the test-tube 37 is pushed upward into the sleeve 36, the short end 38 of the syringe 35 will puncture the membrane 41 which, in part, seals the top end 46 of the test tube 37. The vacuum or low pressure provided inside the test-tube 37 creates a pressure drop which causes fluid to flow downward through the syringe 35 and into the tube 37.

Still referring to FIG. 9, the injection site 13 is preferably equipped with a membrane-type seal 30 similar to the membrane-type seal 41 shown with respect to the test-tube 37. The seals are made from resilient elastomeric material so that the syringe ends 39, 38 may be easily inserted through the seals 30, 41 respectively and thereafter removed. When the syringe end 39 is removed, the seal 30 resumes its original position and reseals itself thereby precluding any leakage of fluid. Hence, when the syringe end 39 is removed from the injection site 13 after a fluid sample is taken (see FIG. 9), no fluid will drip downward through the injection site 13. Further, when the syringe end 38 is removed from the test-tube 37, the seal 41 will reseal itself to prevent any spillage or leakage from the tube 37.

In addition to the collection bag 25, syringe 35, sleeve 36 and test tube 37, the kit may also include a piercing sampler 48 as shown in FIG. 10. The sampler 48 includes a sharp end 49 which includes an aperture 52 through which fluid will pass to the lower end 53 of the sampler. A channel (not shown) connecting the aperture 52 and lower end 53 is narrow enough so that fluid will be provided one drop at a time. Thus, if the technician desires to retrieve only a drop of the liquid contained in the test-tube 37 for purposes of examination on a glass slide 54 (see FIG. 11), the technician simply needs to insert the piercing sampler 48 into the membrane seal 41 disposed at the top end 46 of the test-tube 37 and thereafter invert the test-tube 37 over the glass slide 54. The piercing sampler 48 may be removed and the membrane seal 41 will resume its original shape and sealing effect. In addition, the preferred test-tube 37 will also include a foil-type seal 55 which may be removed (see FIG. 12) so that a wire loop 56 or other apparatus may access the liquid 31 contained within the test-tube 37.

Thus, the present invention can be provided in a variety of forms. First, the improved container 11 as shown in FIGS. 1–4 provides a substantial improvement over the specimen bags known in the art due to the injection site 13 which enables a nurse or technician to withdraw a test sample of fluid 31 from the bag 25 in a safe manner without risking exposure to fluid or spillage of fluid. In addition, a kit may be provided which includes the disposable container 11, a double-ended syringe 35 (with safety cap 47), the sleeve 36 and a test tube 37 (preferably equipped with a membrane-type seal 41). Still further, the kit may include the piercing sampler 48 and may even include a glass slide 54. Finally, all of the above may be included with or without a wire loop 56 (see FIG. 12).

The present invention as illustrated in FIGS. 1–12 also lends itself to an improved method of collecting a test sample of bodily fluid. First, the patient uses the disposable container 11 in the manner illustrated in FIG. 2 and provides a deposit of fluid in the collection bag 25. Then, if the tubular member 14 is equipped with the flaps 17, 18, the patient then closes the tubular member 14 as illustrated in FIG. 3 and hands the disposable container 11 to a technician. The technician (or the patient) will then pull the sleeve 27 upward and over the tubular member 14 prior to sealing the end 29 of the sleeve 27 with a twist-tie 28 or similar sealing mechanism. For example, a zipper-type locking mechanism may be provided at the lower end 29 of the sleeve 27. Then, to obtain a test sample, the technician will insert the long end 39 of the syringe 35 into the injection site 13 as shown in FIG. 7 before inserting vacuumed test-tube 37 over the syringe end 38 as shown in FIGS. 8 and 9. After a sample is withdrawn, the long end 39 of the syringe is removed from the injection site 13, the cap 47 is replaced over the long end 39 of the syringe 35 and a sleeve 36 is pulled off of the test-tube 37. A drop-size sample may be obtained by using a piercing sampler 48 or the foil-top 55 of the test tube 37 may be removed and the entire contents may be examined with a wire loop 56 as shown in FIG. 12.

Although only a limited number of embodiments of the present invention have been illustrated and are described, it will at once be apparent to those skilled in the art that variations may be made within the spirit and scope of the present invention. Accordingly, it is intended that the scope of the invention be limited solely by the scope of the hereafter appended claims and not by any specific wording in the foregoing description.

I claim:

1. A kit for collecting and testing bodily fluids, the kit comprising:
   a disposable container including
   a tubular member having an upper end portion and a lower end portion,
   a valve sealably attached to the lower end portion of the tubular, member,
   a closure means attached to the upper end of the tubular member that is further characterized as including two overlapping opposing flaps attached to the upper end of the tubular member, each flap folding inward, one on top of the other, to substantially close the upper end of the tubular member,
   a collection bag, the bag including an upper portion that is sealably attached to an outer surface of the tubular member and a lower portion for collecting fluid, the lower portion of the collection bag including an injection site for removing samples of fluid from the collection bag, the injection site is further characterized as being an injection tube that sealably passes through the lower end of the collection bag, the injection tube accommodating a membrane, the membrane sealing the injection tube and preventing leakage of fluid through the injection tube, the membrane capable of being punctured by the syringe during removal of a sample from the collection bag, the membrane further being sufficiently resilient so that the membrane is resealed upon the withdrawal of the syringe from the membrane, the injection tube of the injection site also includes a removable cap to protect the membrane prior to the removal of a sample,
   a sleeve including a first open end portion and a second open end portion, the first open end portion being sealably attached to the outer surface of the tubular member between an upper end of the tubular member and the upper portion of the collection bag,
   the second open end portion of the sleeve folding upward over the upper end of the tubular member and being sealable,
   the upper portion of the collection bag, the valve and the second open end of the sleeve combining to provide substantial containment of fluid within the disposable container after fluid is disposed therein;
   means for withdrawing a sample of fluid through the injection site, said means for withdrawing a sample of fluid through the injection site further characterized as including
   a test tube for receiving the fluid sample that is passed through the syringe,
   a test-tube-holding-sleeve having a closed end and an open end, the syringe is sealably attached to a closed end of a test tube-holding sleeve, the open end of the test-tube-holding-sleeve receiving the test tube.

2. A method of collecting a bodily fluid and retrieving a test sample of the bodily fluid, the method comprising the following steps:
   a. depositing the bodily fluid into a disposable container, the disposable container comprising
   a tubular member having an upper end portion and a lower end portion,
   valve means sealably attached to the lower end portion of the tubular member,
   a collection bag, the bag including an upper portion that is sealably attached to an outer surface of the tubular member and a lower portion for collecting fluid, the lower portion of the collection bag including an injection site for removing samples of fluid from the collection bag,
   a sleeve including a first open end portion and a second open end portion, the first open end portion being sealably attached to the outer surface of the tubular member,
   the second open end portion of the sleeve folding upward over the upper end of the tubular member and being sealable,
   the upper portion of the collection bag, which is sealably attached to the tubular member, in combination with the valve means and the second open end portion of the sleeve providing substantial containment of fluid within the disposable container after fluid is disposed therein;
   b. folding the second open end portion of the sleeve upward over the conically-shaped tubular member and sealing the second open end portion of the sleeve;
   c. injecting a first end of a double-end syringe into the injection site; and
   d. inserting a vacuumed test-tube over a second end of the syringe to create a pressure drop across the syringe thereby withdrawing a sample of the bodily fluid through the syringe and into a test tube.

* * * * *